(12) United States Patent
Eiceman et al.

(10) Patent No.: US 10,049,868 B2
(45) Date of Patent: Aug. 14, 2018

(54) APPARATUS FOR DETECTING CONSTITUENTS IN A SAMPLE AND METHOD OF USING THE SAME

(71) Applicant: Rapiscan Systems, Inc., Torrance, CA (US)

(72) Inventors: Gary A. Eiceman, Las Cruces, NM (US); Stephen J. Davila, Pearland, TX (US); Stefan R. Lukow, Hampstead, NH (US); Hartwig Schmidt, Tewksbury, MA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

(21) Appl. No.: 15/370,947

(22) Filed: Dec. 6, 2016

(65) Prior Publication Data

US 2018/0158665 A1    Jun. 7, 2018

(51) Int. Cl.
*H01J 49/40* (2006.01)
*G01N 27/62* (2006.01)
*H01J 49/00* (2006.01)

(52) U.S. Cl.
CPC .......... *H01J 49/401* (2013.01); *G01N 27/622* (2013.01); *H01J 49/0045* (2013.01)

(58) Field of Classification Search
CPC ............... G01N 27/622; G01N 27/624; G01N 30/7233; G01N 30/7206; G01N 33/6803;

(Continued)

(56) References Cited

U.S. PATENT DOCUMENTS 5,491,337 A    2/1996   Jenkins
6,211,516 B1   4/2001   Syage
(Continued)

FOREIGN PATENT DOCUMENTS

AT    303589 T    9/2005
AT    480769 T    9/2010
(Continued)

OTHER PUBLICATIONS

Koeniger, Stormy L. et al, "An IMS-IMS Analogue of MS-MS," Analytical Chemistry, vol. 78, No. 12, Jun. 15, 2006, pp. 4161-4174.
(Continued)

*Primary Examiner* — David A Vanore
(74) *Attorney, Agent, or Firm* — Novel IP

(57) ABSTRACT

An apparatus for detecting constituents in a sample includes first and second drift tubes defining first and second drift regions, and a controllable electric field device within a fragmentation region coupled to the first and second drift tubes. The apparatus also includes a first ion shutter positioned between the first drift and fragmentation regions. The apparatus further includes a control system configured to regulate the first ion shutter, thereby facilitating injection of a selected portion of ions from the first drift region into the fragmentation region. The control system is also configured to regulate the controllable device to modify the selected portion of ions to generate predetermined ion fragments within the fragmentation region, thereby facilitating injection of a selected portion of the predetermined fragmented ions into the second drift region. A method of detecting constituents in a sample is facilitated through such an apparatus.

24 Claims, 4 Drawing Sheets

(58) Field of Classification Search
CPC ...... H01J 49/004; H01J 49/40; H01J 49/0031;
H01J 49/0036; H01J 49/0418; H01J
49/4215; H01J 49/0018; H01J 49/0027;
H01J 49/0059; H01J 49/025; H01J 49/06;
H01J 49/066; H01J 49/164; H01J 49/165;
H01J 49/4265
USPC ................ 250/282, 288, 281, 287, 286, 291
See application file for complete search history.

(56) References Cited

U.S. PATENT DOCUMENTS

| | | | |
|---|---|---|---|
| 6,326,615 B1 | 12/2001 | Syage | |
| 6,329,653 B1 | 12/2001 | Syage | |
| 6,630,664 B1 | 10/2003 | Syage | |
| 6,642,513 B1 | 11/2003 | Jenkins | |
| 6,690,005 B2 | 2/2004 | Jenkins | |
| 6,708,572 B2 | 3/2004 | Jenkins | |
| 6,737,642 B2 | 5/2004 | Syage | |
| 6,765,198 B2 | 7/2004 | Jenkins | |
| 6,797,943 B2 | 9/2004 | Lösch et al. | |
| 6,815,670 B2 | 11/2004 | Jenkins | |
| 6,822,224 B2 | 11/2004 | Guevremont | |
| 6,831,273 B2 | 12/2004 | Jenkins | |
| 6,840,122 B1 | 1/2005 | Jenkins | |
| 6,897,434 B1 | 5/2005 | Kumar | |
| 6,897,437 B2* | 5/2005 | Fuhrer | G01N 27/622 250/282 |
| 7,047,829 B2 | 5/2006 | Napoli | |
| 7,109,476 B2 | 9/2006 | Hanold | |
| 7,119,342 B2 | 10/2006 | Syage | |
| 7,141,786 B2 | 11/2006 | McGann | |
| 7,161,144 B2 | 1/2007 | Syage | |
| 7,196,325 B2 | 3/2007 | Syage | |
| 7,253,727 B2 | 8/2007 | Jenkins | |
| 7,299,710 B2 | 11/2007 | Syage | |
| 7,338,638 B2 | 3/2008 | McGann | |
| 7,401,498 B2 | 7/2008 | Syage | |
| 7,448,248 B2 | 11/2008 | Carey | |
| 7,456,393 B2 | 11/2008 | Napoli | |
| 7,528,367 B2 | 5/2009 | Haigh | |
| 7,541,577 B2 | 6/2009 | Davenport | |
| 7,594,422 B2 | 9/2009 | Perry | |
| 7,594,447 B2 | 9/2009 | Napoli | |
| 7,663,099 B2 | 2/2010 | Reda | |
| 7,721,588 B2 | 5/2010 | Perry | |
| 7,851,743 B2 | 12/2010 | Okumura | |
| 7,856,898 B2 | 12/2010 | Carey | |
| 7,880,137 B2 | 2/2011 | McGann | |
| 7,932,489 B2 | 4/2011 | Atkinson et al. | |
| 8,106,352 B2 | 1/2012 | Ching | |
| 8,161,830 B2 | 4/2012 | Boudries | |
| 8,186,234 B2 | 5/2012 | Syage | |
| 8,288,735 B2 | 10/2012 | Syage | |
| 8,384,024 B2 | 2/2013 | Miller et al. | |
| 8,402,842 B2 | 3/2013 | Syage | |
| 8,434,375 B1 | 5/2013 | Syage | |
| 8,436,299 B2 | 5/2013 | Atkinson et al. | |
| 8,614,582 B2 | 12/2013 | Syage | |
| 8,686,355 B2 | 4/2014 | Patterson | |
| 8,723,111 B2 | 5/2014 | Syage | |
| 8,754,366 B2 | 6/2014 | Burchfield et al. | |
| 8,857,278 B2 | 10/2014 | Syage | |
| 8,866,073 B2 | 10/2014 | Goedecke | |
| 8,921,778 B2 | 12/2014 | Atkinson et al. | |
| 8,952,327 B2 | 2/2015 | Patterson | |
| 9,012,840 B2 | 4/2015 | Bateman et al. | |
| 9,147,565 B1 | 9/2015 | Goedecke | |
| 9,354,153 B2 | 5/2016 | Syage | |
| 9,482,655 B2 | 11/2016 | Vilkov | |
| 9,528,969 B2 | 12/2016 | Shaw | |
| 9,558,924 B2 | 1/2017 | Syage | |
| 9,683,981 B1 | 6/2017 | Vilkov | |
| 9,689,857 B1 | 6/2017 | Vilkov | |
| 9,726,655 B2 | 8/2017 | Syage | |
| 9,766,218 B2 | 9/2017 | Lai | |
| 9,789,434 B1 | 10/2017 | Lai | |
| 2003/0146377 A1* | 8/2003 | Miller | G01N 27/624 250/286 |
| 2004/0108452 A1* | 6/2004 | Graber | G01N 33/6803 250/281 |
| 2005/0035284 A1* | 2/2005 | Schultz | H01J 49/0031 250/287 |
| 2005/0127289 A1* | 6/2005 | Fuhrer | H01J 49/025 250/288 |
| 2005/0253059 A1 | 11/2005 | Goeringer et al. | |
| 2007/0176092 A1* | 8/2007 | Miller | G01N 27/624 250/288 |
| 2009/0294644 A1* | 12/2009 | Belov | G01N 27/622 250/282 |
| 2010/0090101 A1* | 4/2010 | Schultz | H01J 49/0418 250/282 |
| 2010/0108879 A1 | 5/2010 | Bateman et al. | |
| 2011/0057096 A1 | 3/2011 | Fernandez de la Mora et al. | |
| 2011/0127417 A1* | 6/2011 | Ibrahim | H01J 49/004 250/282 |
| 2012/0153140 A1* | 6/2012 | Makarov | G01N 27/622 250/282 |
| 2014/0346339 A1 | 11/2014 | Wu et al. | |
| 2016/0005581 A1* | 1/2016 | Graichen | G01N 27/622 250/282 |
| 2016/0079048 A1 | 3/2016 | Bonner et al. | |
| 2016/0274059 A1* | 9/2016 | Hoyes | G01N 27/622 |
| 2016/0282304 A1 | 9/2016 | Vilkov | |
| 2017/0044619 A1* | 2/2017 | Rose | C12Q 1/6886 |
| 2017/0103880 A1 | 4/2017 | Syage | |
| 2017/0213715 A1 | 7/2017 | Davila | |
| 2017/0261483 A1 | 9/2017 | Vilkov | |
| 2017/0261484 A1 | 9/2017 | Vilkov | |
| 2017/0284977 A1 | 10/2017 | Rogers | |
| 2017/0299550 A1* | 10/2017 | Wang | G01N 27/622 |
| 2017/0309463 A1 | 10/2017 | Vilkov | |

FOREIGN PATENT DOCUMENTS

| | | |
|---|---|---|
| CA | 2153371 C | 3/1999 |
| CA | 2436256 C | 6/2007 |
| CA | 2382823 C | 11/2007 |
| CA | 2362449 C | 10/2008 |
| CA | 2411532 C | 4/2010 |
| CA | 2285153 C | 5/2010 |
| CA | 2479875 C | 2/2011 |
| CA | 2538709 C | 2/2013 |
| CA | 2790430 A1 | 3/2013 |
| CA | 2807894 A1 | 9/2013 |
| CA | 2620405 C | 7/2014 |
| CA | 2548177 C | 9/2014 |
| CA | 2844222 A1 | 9/2014 |
| CA | 2845959 A1 | 9/2014 |
| CA | 2688352 C | 6/2015 |
| CA | 2644937 C | 11/2015 |
| CA | 2904479 A1 | 3/2016 |
| CA | 2910780 A1 | 4/2016 |
| CA | 2913931 A1 | 6/2016 |
| CA | 2915785 A1 | 6/2016 |
| CA | 2924580 A1 | 9/2016 |
| CA | 2647651 C | 11/2016 |
| CA | 2738053 C | 5/2017 |
| CA | 2959791 A1 | 9/2017 |
| CA | 2959796 A1 | 9/2017 |
| CA | 2962154 A1 | 9/2017 |
| CA | 2964147 A1 | 10/2017 |
| CN | 100445767 C | 12/2008 |
| CN | 103308590 A | 9/2013 |
| CN | 105738461 A | 7/2016 |
| CN | 107037114 A | 8/2017 |
| CN | 107167334 A | 9/2017 |
| CN | 107167335 A | 9/2017 |
| CN | 107271254 A | 10/2017 |
| DE | 69528418 T2 | 1/2003 |
| DE | 69926965 T2 | 6/2006 |
| EP | 2368102 A2 | 9/2011 |
| EP | 2637013 A2 | 9/2013 |

(56) References Cited

FOREIGN PATENT DOCUMENTS

| | | |
|---|---|---|
| EP | 2778650 A2 | 9/2014 |
| EP | 2778669 A1 | 9/2014 |
| EP | 2884254 A1 | 6/2015 |
| EP | 3015858 A1 | 5/2016 |
| EP | 3032570 A2 | 6/2016 |
| EP | 3040717 A1 | 7/2016 |
| EP | 1938078 B1 | 3/2017 |
| EP | 1297554 B1 | 4/2017 |
| EP | 3182111 A1 | 6/2017 |
| ES | 2183855 | 4/2003 |
| FR | 692712 A | 11/1930 |
| GB | 992782 A | 5/1965 |
| GB | 2075578 A | 11/1981 |
| GB | 2496286 A | 5/2013 |
| GB | 2536076 A | 9/2016 |
| JP | 3045655 B2 | 5/2000 |
| WO | 2012148836 A1 | 11/2012 |

OTHER PUBLICATIONS

Eiceman, G. A., "History of Tandem Ion Mobility Spectrometry At or Near Ambient Pressure," New Mexico State University, Mar. 2014, retrieved from website http://ionmobility.nmsu.edu/history/ (10 pages).

International Search Report for PCT/US17/64702, dated Jan. 8, 2018.

\* cited by examiner

APPARATUS FOR DETECTING CONSTITUENTS IN A SAMPLE AND METHOD OF USING THE SAME

BACKGROUND

The embodiments described herein relate generally to ion mobility spectrometer (IMS) systems and ion trap mobility spectrometer (ITMS) systems and, more particularly, to IMS and ITMS detection systems for enhancing detection of materials of interest through enhanced information of fragmented ions.

At least some known spectrometric detection devices include a time-of-flight (TOF) ion mobility spectrometer (IMS) detection system and a TOF ion trap mobility spectrometer (ITMS) detection system. Such TOF-IMS and -ITMS detection systems are used to detect trace amounts of materials of interest, e.g., residues, in the presence of interfering substances in collected samples. In at least some known IMS and ITMS systems, ions are generated in an ionization chamber to increase the ion population therein and a retaining grid or an ion gate is maintained at a potential to induce a retention field and reduce the potential for ion leakage from the chamber. The ions are "pulsed" from the ionization chamber into a drift region through the retaining grid or ion gate. The ions are transported through the drift region to a collector electrode using an electric field. Signals representative of the ion population at the collector electrode are generated and transmitted to an analysis instrument and/or system to determine the constituents in the collected gas samples. Based on an ions' mass, charge, size, and shape, the ion mobility determines the migration time through the drift region which is characteristic of different ions, leading to the ability to distinguish different analyte species.

However, many known drift tubes of IMS and ITMS systems have a limited resolving power. As peaks generated by ions from different compounds share similar drift times, some of the interferences, including benign substances, have the same drift times as the analyte compounds of interest associated with an increasing number of threats programmed into the detection library and, therefore, create false alarms. A number of methods and apparatus have been used to characterize the ions of interest and to decrease the false alarm rate which is addressed by the concept of the reactive drift tubes.

One method proposed to decrease the false alarm rate is fragmentation, i.e., the dissociation of energetically unstable molecular ions to form ion fragments of a molecule that induce a pattern in the mass spectrum or mobility spectrum used to determine structural information of the original molecule. Fragmentation can be achieved through a variety of means, including fragmentation induced by collision induced dissociation (CID) with selected gases injected into the flow path of the apparatus, fragmentation induced through a set of electrodes capable of generating electric fields with sufficiently high electric field strength to thermally form disassociated products, dissociation through laser that, depending on the required wavelength and molecules to be dissociated, uses one of photodissociation, infrared multiphoton dissociation, and thermal dissociation. Further methods of fragmentation include electron capture and transfer methods through injection of active chemicals.

Some known IMS and ITMS systems use ion dissociation through a high-voltage radio-frequency (HV RF) unit positioned within the drift tube. However, such IMS and ITMS systems lack the selection of ions to be fragmented, e.g., through a second ion shutter before the HV-RF unit. Therefore, most of the ions to be fragmented and the fragmented ions enter the second portion of the drift region without any screening, regardless of the chemical makeup of the fragmented ions. As such, the assignment of the fragment ions to spectral patterns is complex with little to no discrimination. The results may be ambiguous because the ability to discern the identity of the resulting fragments is limited since the ions to be dissociated are not separated from the other ions. In some of these known IMS and ITMS systems, operation at reduced pressures is one attempt of reducing the number of ion collisions and thus reducing the number of fragments to generate a more simplistic raw data stream, but the simplicity of the IMS and ITMS techniques is compromised by adding the additional hardware, such as vacuum chambers and pumps.

Some other known IMS and ITMS systems include a plurality of tandem drift tubes with ion control grids therebetween, where one of the drift tubes includes a fragmentation device. Such tandem drift tube devices are configured to select ions from a first drift tube through an ion control grid for introduction into a second drift tube for fragmentation through one of laser irradiation and vapor injection to promote selective reactions and additional analytical selectivity. However, such mechanisms substantially form adducts with the selected ions that are transferred to a third drift tube through another ion control grid for characterization therein. Also, uncontrolled movement of sample neutrals between mobility regions facilitates ion molecule reactions in the drift regions that further complicate the interpretation of the resultant spectra.

BRIEF DESCRIPTION

In one aspect, an apparatus for detecting constituents in a sample is provided. The apparatus includes a first drift tube defining a first drift region, a second drift tube defining a second drift region, and a controllable electric field device coupled to the first drift tube and the second drift tube. The controllable electric field device at least partially defines a fragmentation region. The apparatus also includes a first ion shutter positioned between the first drift region and the fragmentation region. The apparatus also includes a control system coupled to the controllable electric field device and the first ion shutter. The control system is configured to facilitate injection of a selected portion of the predetermined fragmented ions into the second drift region. The control system includes a processor and is also configured to regulate the first ion shutter a first predetermined temporal period, thereby facilitating injection of a selected portion of ions from the first drift region into the fragmentation region. The control system is further configured to regulate the controllable electric field device to modify the selected portion of ions to generate predetermined ion fragments within the fragmentation region.

In another aspect, a method of detecting constituents in a sample is provided. The method includes channeling a sample gas stream to be tested for constituents into an ionization region, generating a plurality of ions in the ionization region, and injecting at least a portion of the ions from the ionization region into a first drift region. The method also includes injecting a selected portion of ions from the first drift region into a fragmentation region including regulating a first ion shutter a first predetermined temporal period, where the first ion shutter is positioned between the first drift region and the fragmentation region. The method further includes modifying the selected portion of ions, thereby generating predetermined ion fragments within the fragmentation region including regulating a controllable electric field device positioned within the fragmentation region.

DRAWINGS

FIG. 1 is a schematic view of an exemplary ion trap mobility spectrometer (ITMS) detection system;

FIG. 2 is a schematic view of an alternative ion trap mobility spectrometer (ITMS) detection system;

FIG. 3 is a graphical view of exemplary spectra that may be produced using the ITMS detection systems shown in FIGS. 1 and 2; and FIG. 4 is a graphical view of additional exemplary spectra that may be produced using the ITMS detection systems shown in FIGS. 1 and 2.

DETAILED DESCRIPTION

The embodiments described herein provide a cost-effective system and method for improving detection of materials of interest from an object or person. The systems and methods described herein use a detector having two sequentially arranged drift tubes which are separated by shutters facilitating ions of a user-selected, i.e., library-defined drift time to be introduced into the second drift tube whereas other ions of a different mobility are discarded as needed. The tandem reactive IMS and ITMS devices disclosed herein facilitate multiple opportunities to isolate ions of interest including ion separation and selection in the first drift tube, predetermined modification through fragmentation with a controllable electric field, and selected transmission into the second drift tube ultimately ending with specific identification of the ions. Regulation of the electric field strength and temperature analyte ions from one compound may dissociate and form dissociation products that can further be characterized, while ions from another compound may dissociate as well but form different products or may even not dissociate at all. As such, this dissociation information is important for providing another dimension of characterizing the mobility of ions by their stability and their dissociation products which provides additional confidence in the presence or absence of peaks that facilitates determining if an alarm could be generated or rejected. The results are more easily interpreted and provide more definitive information that can be used for the characterization of ions since only ions of a particular drift time are exposed to the high electric field and the associated fragmentation. Consequently substantially all dissociation products detected in the second drift tube originate from the ions selected from the first drift tube and subsequently fragmented. Moreover, the additional optional introduction of dopants facilitates further modification of the selected ions through chemical reactions with or without dissociation. As such, the systems described herein facilitate an additional level of selectivity that dramatically reduces the false alarm rate from that observed on traditional IMS systems. Therefore, the portable mobility spectrometers described herein facilitate substance analysis with higher confidence while maintaining atmospheric pressure operation.

Figure 1:
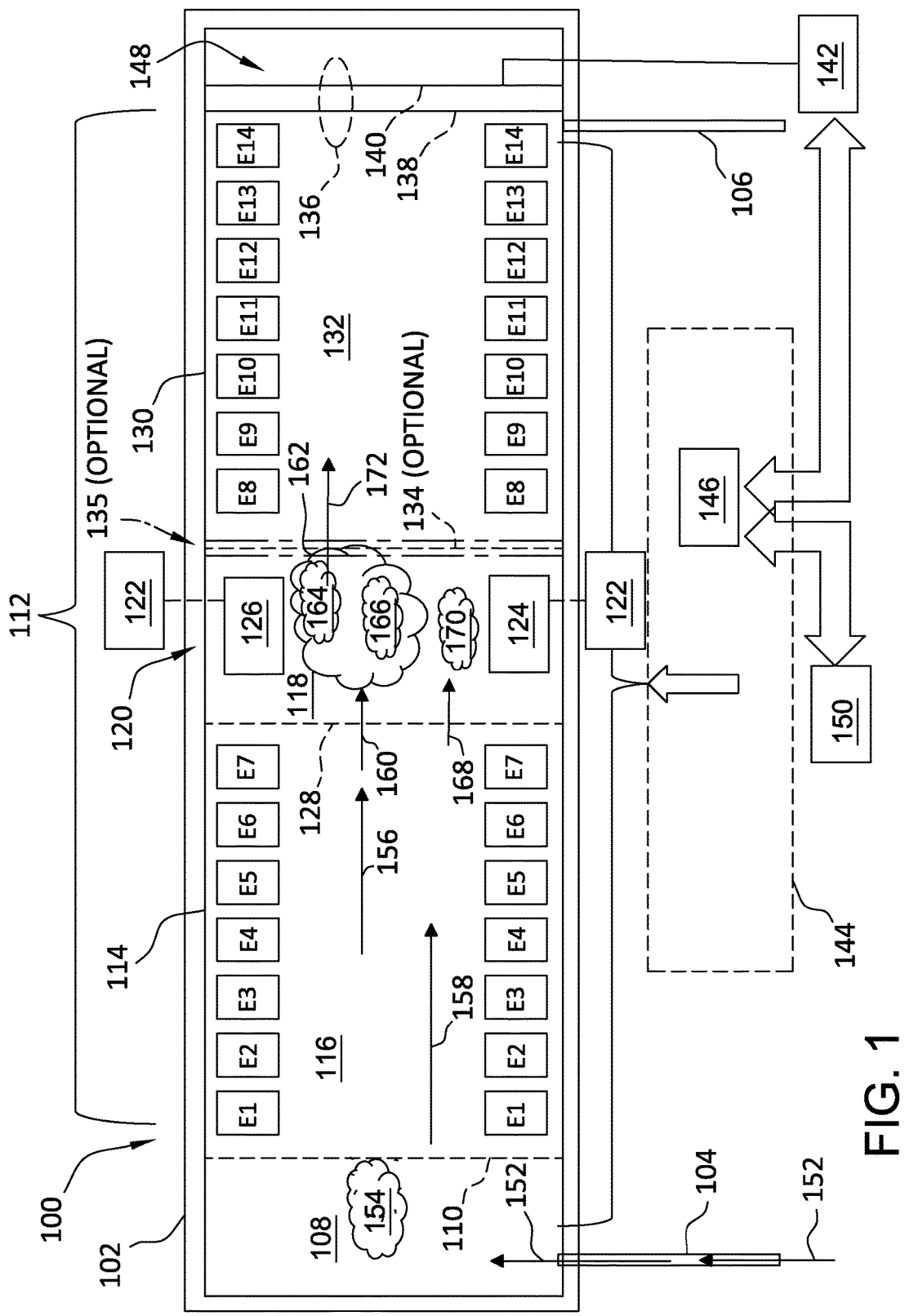
FIGS. 1-4 show exemplary embodiments of the systems and methods described herein.

FIG. 1 is a schematic view of an exemplary time-of-flight (TOF) ion trap mobility spectrometer (ITMS) detection system 100 (not drawn to scale). ITMS detection system 100 includes a casing 102. ITMS detection system 100 also includes a gas inlet tube 104 and a gas outlet tube 106 coupled to casing 102. In the exemplary embodiment, casing 102 includes an ion trap reactor 108 coupled in flow communication with gas inlet tube 104. Ion trap reactor 108 includes an ionizing source material (not shown), e.g., and without limitation, nickel-63 ($^{63}$Ni) that emits low-energy beta- (β-) particles. Alternatively, any ionizing source or ionizing source material that enables operation of ITMS detection system 100 as described herein is used. ITMS detection system 100 further includes a retaining grid 110 extending over an outlet end of ion trap reactor 108.

Casing 102 further defines a tandem reactive dual drift tube and dual shutter configuration 112. Configuration 112 includes a first drift tube 114 defining a first drift field region 116 coupled in flow communication with ion trap reactor 108. Configuration 112 further includes a series of sequential annular electrodes E1, E2, E3, E4, E5, E6, and E7 extending about first drift field region 116. Configuration 112 also includes a fragmentation region 118 at least partially defined by casing 102. Fragmentation region 118 facilitates predetermined modifications of ions received from first drift field region 116 through fragmentation with a controllable electric field generated by an electric field generation device 120 that includes a high-voltage radio-frequency (HV RF) unit 122 and electrodes 124 and 126 spaced from each other across the diameter of fragmentation region 118. Electrodes 124 and 126 are any devices that enable operation of ITMS detection system 100 through production of a strong electric field, such devices including, but not limited to, wire grids and other metal structures that generate sufficient field strength. Electric field generation device 120 generates electric fields of sufficient strengths and frequencies to modify ions therein (discussed further below).

Also, in the exemplary embodiment, configuration 112 further includes a first ion shutter 128 that at least partially defines first drift field region 116 and fragmentation region 118 when energized and facilitates flow communication between regions 116 and 118 when de-energized. In addition, configuration 112 includes a second drift tube 130 defining a second drift field region 132. Configuration 112 also includes a series of sequential annular electrodes E8, E9, E10, E11, E12, E13, and E14 extending about second drift field region 132. Second drift field region 132 receives fragmented ions from fragmentation region 118. In some embodiments, configuration 112 further includes an optional second ion shutter 134 that at least partially defines second drift field region 132 and fragmentation region 118 when energized and facilitates flow communication between regions 118 and 132 when de-energized. In other embodiments, rather than second ion shutter 134, configuration 112 further includes an optional ion trap 135 similar in design, construction, and operation as ion trap reactor 108. Such ion trap 135 positioned between fragmentation region 118 and second drift field region 132 is configured to provide similar operational results as second ion shutter 134, i.e., release fragmented ions into second drift tube 130 as an alternative to using a shutter grid.

ITMS detection system 100 also includes an ion collector 136 that includes a collector shield grid, i.e., an aperture grid 138 and a collector electrode 140, e.g., a Faraday plate positioned just downstream of aperture grid 138. Collector electrode 140 is coupled to a spectral analysis device 142 that includes at least one current-to-voltage amplifier (not shown). ITMS detection system 100 further includes an ITMS control system 144 that includes a processing device 146. ITMS control system 144 is operatively coupled to ion trap reactor 108, retaining grid 110, sequential annular electrodes E1-E7, electric field generation devices 120, first ion shutter 128, second ion shutter 134 (if installed), second ion trap 135 (if installed), E8-E14, aperture grid 138, collector electrode 140, and spectral analysis device 142. Casing 102 also defines a collector region 148 coupled in flow communication with second drift field region 132 and gas outlet tube 106.

As used herein, the terms "processor" and "processing device" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Also, as used herein, the terms "software" and "firmware" are interchangeable, and include any computer program stored in memory for execution by personal computers, workstations, clients and servers.

Further, as used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Furthermore, as used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

Processing device 146 and other processors (not shown) as described herein process information transmitted from a plurality of electrical and electronic devices that include, without limitation, spectral analysis device 142 and feedback devices (not shown) within ITMS detection system 100. Memory devices (not shown) and storage devices (discussed further below) store and transfer information and instructions to be executed by processing device 146. Such memory devices and storage devices can also be used to store and provide temporary variables, static (i.e., non-volatile and non-changing) information and instructions, or other intermediate information to processing device 146 during execution of instructions by processing device 146. Instructions that are executed include, but are not limited to, analysis of signals transmitted from spectral analysis device 142. The execution of sequences of instructions is not limited to any specific combination of hardware circuitry and software instructions. ITMS detection system 100 also includes a data storage device 150 coupled to processing device 146. Data storage device 140 stores the data generated by processing device 146, such data also retrievable through processing device 146.

In operation, a collection device (not shown) is coupled to gas inlet tube 104 and collects gaseous samples 152 from an object of interest (not shown). In some embodiments, rather than gaseous samples, inlet tube 104 channels particulate samples that are then vaporized to generate gaseous samples 152. Gaseous samples 152 are channeled to the diffuser region portion of ion trap reactor 108 for expanding gaseous samples 152 prior to entry into the ionization chamber portion of ion trap reactor 108. $^{63}$Ni emits low-energy β-particles into ion trap reactor 108 and the β-particles ionize samples 152 while in the gaseous phase, thereby forming positive ions, negative ions, and free electrons. Ion trap reactor 108 is substantially a field-free region. Therefore, increasing a population density of the ions and electrons within ion trap reactor 108 is facilitated as a function of the flux of β-particles. As the ions are being generated in ion trap reactor 108 to increase the stored ion population 154 therein, retaining grid 110 is maintained at a slightly greater potential than the potential of ion trap reactor 108 to induce a retention field and reduce the potential for ion leakage from ion trap reactor 108. An electric field is then induced across ion trap reactor 108 and, depending on the polarity of the induced electric field, the positive ions or the negative ions are pulsed from ion trap reactor 108, through a high-voltage "kickout pulse", and injected into first drift field region 116 through retaining grid 110. The ions of the opposite polarity are attracted to the walls of ion trap reactor 108 and are discharged there. The pulses are controlled through ITMS control system 144.

First drift field region 116 extends from retaining grid 110 to first ion shutter 128. For those systems that use negative ions, annular electrodes E1 through E7 are energized to voltages that are sequentially less negative between retaining grid 110 to first ion shutter 128, thereby inducing a constant positive field. Motion is induced in the negative ions from the initial pulse in ion trap reactor 108 and the ions are channeled through first drift field region 116 to first ion shutter 128. First ion shutter 128 induces a voltage that is less negative than the voltage of electrode E1 and is more negative than the voltage of electrode E7. ITMS control system 144 regulates the velocities of the ions injected from ion trap reactor 108 as they drift through first drift field region 116 toward first ion shutter 128 such that a selected portion 156 of ions injected into region 116 arrive at shutter 128 at a predetermined time, while a substantial amount of a non-selected portion 158 of ions arrive later due to the slower velocities or faster (not shown) due to the higher velocities. As such, ITMS control system 144 regulates the voltage of first ion shutter 128 for a first predetermined temporal period, thereby injecting a substantial amount 160 of the selected portion 156 of ions from first drift field region 116 into fragmentation region 118. A significant amount of the non-selected portion 158 of ions are not permitted to transit through first ion shutter 128 when the voltage is again adjusted by ITMS control system 144 to block such ions and molecules that are subsequently discarded, thereby reducing injection of the non-selected portion of ions and into fragmentation region 118.

Also, in operation, ITMS control system 144 regulates electric field generation device 120 to modify the selected portion of ions, thereby generating predetermined ion fragments 162 within fragmentation region 118 through regulating a voltage and frequency of the controllable electric field generated between electrodes 124 and 126. The electric field dissociates a first portion of the selected portion 160 of ions injected into fragmentation region 118 into a first portion 164 of the predetermined ion fragments for further transmission to second field drift region 132. Fragmentation of selected ions 162 generates ion fragments 164 that have a different mobility from unmodified ions 166 that generate different peaks on the associated output spectrum. As such, fragmentation facilitates distinguishing between two different, but intermingled ion populations that would otherwise have similar mobilities, since the modified versions of these fragment ions 164 will have dissimilar mobilities from those of unmodified ions 166.

Further, in operation, at least some of those ions 168 of the non-selected portion of ions 158 that made it into fragmentation region 118 are also modified to further distinguish the resultant dissociated non-selected ions 170 from the predetermined ion fragments 162 under consideration due to the different mobilities. The dissociated non-selected ions 170 are discarded. In alternative embodiments, none of the non-selected ions 158 are dissociated into fragments, but are discarded regardless.

Moreover, for those embodiments that include optional second ion shutter 134, in operation, the selected ion fragments under consideration 164 arrive at second ion shutter 134 at different times than most of the other ions, molecules, and fragments due to the different mobilities. As such, ITMS control system 144 regulates the voltage of second ion shutter 134 for a second predetermined temporal period, thereby injecting a substantial amount 172 of the selected portion 164 of the predetermined fragmented ions from fragmentation region 118 into second drift field region 132. A significant amount of the non-selected portion of ions 170 and fragments 166 are not permitted to transit through second ion shutter 134 when the voltage is again adjusted by ITMS control system 144 to block such ions 170 and fragments 166 that are subsequently discarded, thereby reducing injection of the non-selected portion of ions 158 into second drift field region 132.

Second drift field region 132 extends from a region between the downstream side of electrodes 124 and 126, or second ion shutter 134 (if installed), to collector region 148 defined by ion collector 136 and casing 102. Collector electrode 140 is positioned on the opposite side of drift field region 112 from electrodes 124 and 126, or second ion shutter 134 (if installed), and is held at, or near, a ground potential. For those systems that use negative ions, annular electrodes E8 through E14 are energized to voltages that are sequentially less negative than between electrodes 124 and 126, or second ion shutter 134 (if installed), to collector electrode 140, thereby inducing a constant positive field. For those embodiments that include optional ion trap 135 rather than optional second ion shutter 134, such ion trap 135 positioned between fragmentation region 118 and second drift field region 132 is configured to provide similar operational results as second ion shutter 134, i.e., release fragmented ions into second drift tube 130 as an alternative to using a shutter grid.

For such embodiments with second ion shutter 134, ITMS control system 144 regulates the voltage of second ion shutter 134 for a second predetermined temporal period, thereby injecting a substantial amount 172 of the selected portion 164 of fragmented ions from fragmentation region 118 into second drift field region 132. For those embodiments that include optional ion trap 135 rather than optional second ion shutter 134, such ion trap 135 positioned between fragmentation region 118 and second drift field region 132 is configured to provide similar operational results as second ion shutter 134, i.e., release fragmented ions into second drift tube 130 as an alternative to using a shutter grid. Motion is induced in the negative ions through the graduated potential along second field drift region 132. As such, ITMS control system 144 regulates the velocities of the selected portion 172 of the predetermined fragmented ions 164 injected from fragmentation region 118 as they drift through second drift field region 132 toward collector electrode 140. The selected portion 172 of the predetermined fragmented ions 164 injected into region 132 arrive at collector electrode 140 at a predetermined time, while any remaining non-selected ions 170 and ion fragments 166 are expected to arrive at a different drift time due to the different velocities. A significant amount of the non-selected portion of ions 170 and ion fragments 166 are not permitted to transit through second ion shutter 134 (or ion trap 135) when the voltage is again adjusted by ITMS control system 144 to block non-selected ions 170 and ion fragments 166 that are subsequently discarded, thereby reducing injection of the non-selected 170 portion of ions and ion fragments 166 into second field drift region 132.

Therefore, in operation, with, or without second ion shutter 134 (and, similarly, with or without ion trap 135), the selected portion 172 of the predetermined fragmented ions 164 drift through second field drift region 132 to collector electrode 140 through aperture grid 138. Aperture grid 138 induces a voltage that is less negative that the voltage of electrode E8 and is more negative than the voltage of collector electrode 140 that is maintained at substantially ground potential. Signals representative of the ion population at collector electrode 140 are generated and transmitted to spectral analysis device 142 to determine the constituents in collected gas samples 152, and a detection spectrum representative of the ion or fragment ions detected at collector electrode 140 through spectral analysis device 142 coupled to collector electrode 140.

The exemplary embodiment as described above is directed to an ITMS detection system 100 configured to use negative ions. However, in some embodiments, ITMS detection system 100 is configured to use positive ions. In such embodiments, the electric field induced across ion trap reactor 108 has a polarity to "kick out" the positive ions rather than the negative ions such that the positive ions are pulsed from ion trap reactor 108 through the high-voltage "kickout pulse", and injected into first drift field region 116 through retaining grid 110. The ions of the opposite polarity are attracted to the walls of ion trap reactor 108 and are discharged there. Motion is induced in the positive ions from the initial pulse in ion trap reactor 108. Also, in such circumstances, annular electrodes E1 through E7 are energized to voltages that are sequentially less positive between retaining grid 110 to first ion shutter 128 to facilitate inducing motion in the positive ions such that the ions are channeled through first drift field region 116 to first ion shutter 128. First ion shutter 128 induces a voltage that is less positive than the voltage of electrode E1 and is more positive than the voltage of electrode E7. The remainder of ITMS detection system 100 is further configured for positive ions rather than negative ions and operation thereof is executed accordingly.

Figure 2:
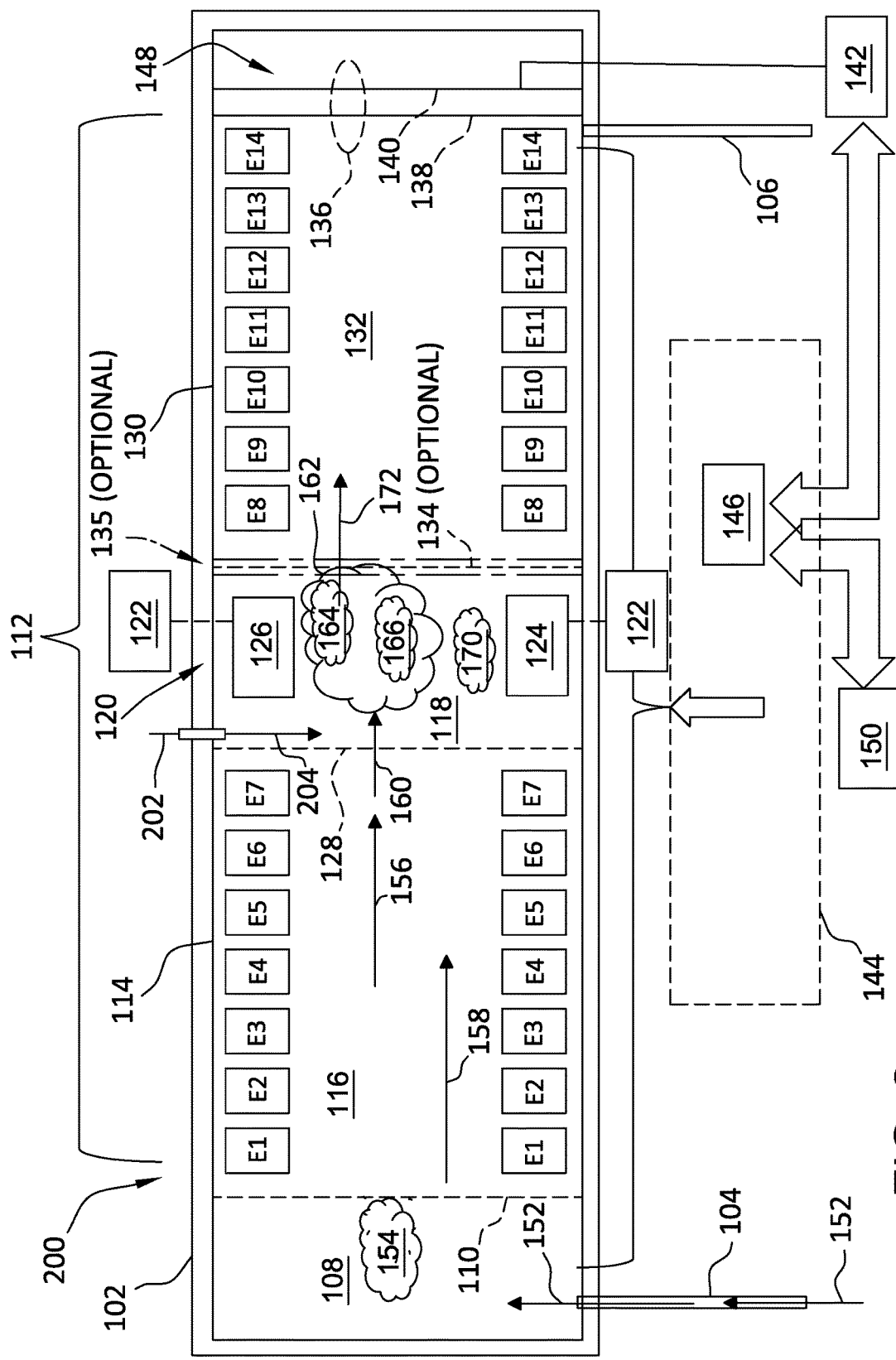

FIG. 2 is a schematic view of an alternative ion trap mobility spectrometer (ITMS) detection system 200 (not drawn to scale). System 200 is similar to system 100 (shown in FIG. 1) with the difference that system 200 includes a dopant injection system 202 coupled in flow communication with fragmentation region 118. Some dopants further enhance the specificity of identification of substances, for example, and without limitation, some typical dopants used in trace detection of explosives are chlorinated compounds, e.g., in a negative ion mode, and without limitation, dichloromethane, hexachloroethane, and chloroform, and, in positive ion modes, and without limitation, acetone and ammonia-based compounds, e.g., ammonium carbamate, and anhydrous ammonia. Therefore, in operation of system 200, a dopant 204 is injected into fragmentation region 118 and at least a portion of injected dopant 204 is mixed with the selected portion of ions 160 from first drift field region 116. Operation of system 200 is similar to that of system 100 as described above, with the primary difference of the dopant altering the population of predetermined fragmented ions 164 and 172 with constituents including, without limitation, adducts (not shown).

TOF ion mobility spectrometer (IMS) detection systems (not shown) are similar to ITMS detection systems 100 and 200 with one difference of the IMS detections systems is that they do not include ion trap features through a retaining grid that is maintained at a relatively constant voltage to trap the ions in the ionization chamber. Rather, IMS detection systems include an ion gate device (sometimes referred to as an ion shutter), e.g., a Bradbury-Nielsen gate. Similar to retaining grid 110 of systems 100 and 200, as the ions are being generated in the IMS ionization region to increase the ion current therein, the ion gate device is maintained at a relative voltage great enough to substantially prevent ion current transmitting into the adjacent drift region. The relative voltage difference between the ion gate device is then temporarily removed and the stored ions are pulsed from the ionization region into the drift region through the ion gate device. The temporal period of gate de-energization is predetermined. The voltage applied of the ion gate device is then re-established, thereby substantially halting ion entry from the ionization region into the drift region. Therefore, rather than pulsing the ions through a consistently energized retaining grid as is done for ITMS systems 100 and 200, in the IMS systems the ion gate is temporarily de-energized.

Figure 3:
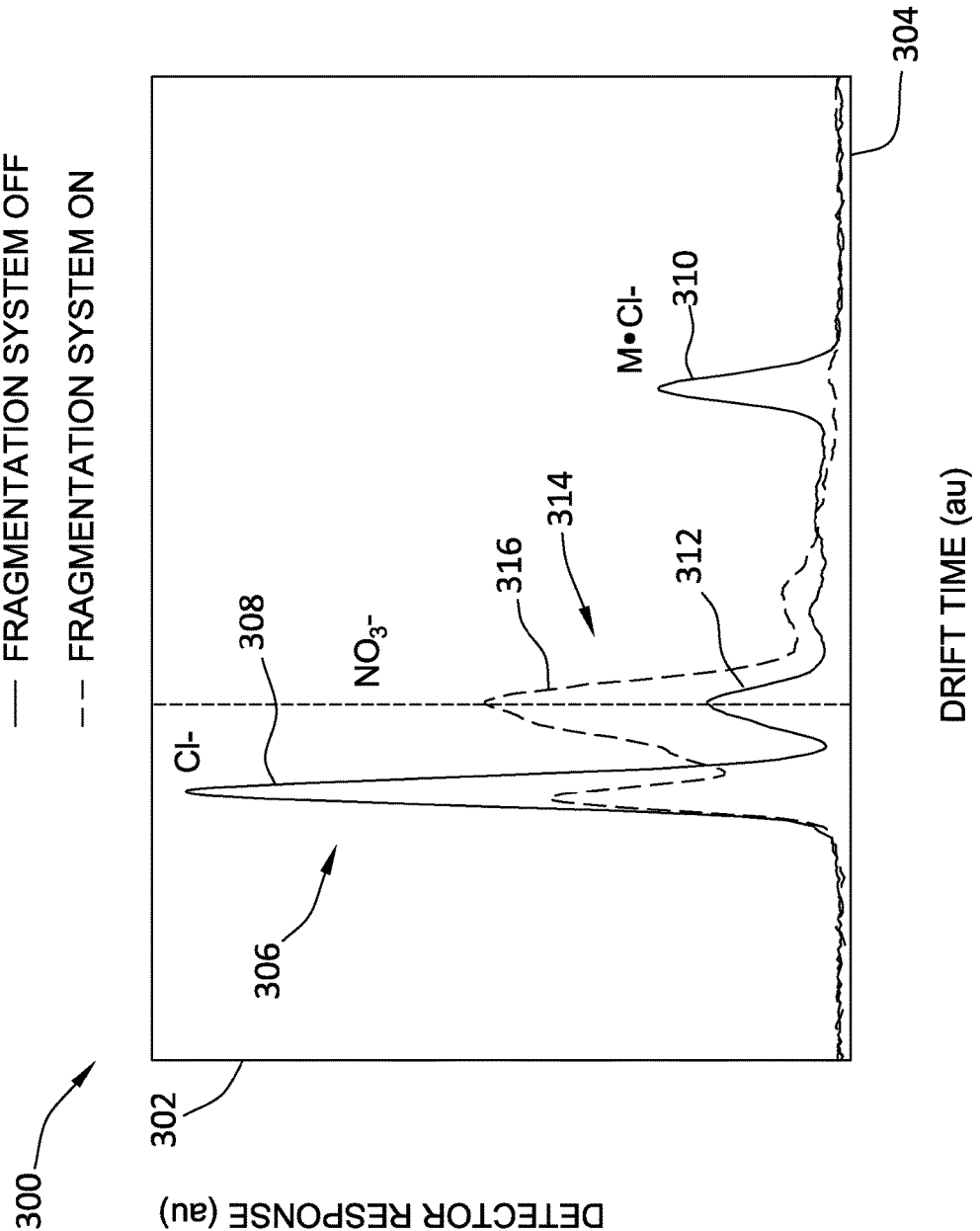

FIG. 3 is a graphical view, i.e., graph 300 of exemplary spectra that may be produced using ITMS detection systems 100 and 200 (shown in FIGS. 1 and 2, respectively). Graph 300 includes a y-axis 302 representative of ion intensity, i.e., detector response in arbitrary units (au). Also, graph 300 includes an x-axis 304 representative of drift time in arbitrary units (au). In the exemplary embodiment, a sample of ethylene glycol dinitrate (EGDN) [$C_2H_4(ONO_2)_2$], a common constituent of explosive devices, is introduced into IMS detection system 200, system 200 including tandem reactive drift tube configuration 112 (shown in FIGS. 1 and 2).

Graph 300 includes a first trace 306 representing a spectral analysis of the EGDN sample with the fragmentation system off, i.e., electric field generation device 120 in fragmentation region 118 (both shown in FIGS. 1 and 2) removed from service. First trace 306 includes a chloride ion ($Cl^-$) peak 308 and a M.$Cl^-$ adduct peak 310. While peak 308 is a dopant peak, peak 310 may indicate the presence of EGDN (EGDN*$Cl^-$). A peak 312 may indicate the presence of trace amounts of $NO_3^-$.

Graph 300 also includes a second trace 314 representing a spectral analysis of the EGDN sample with the fragmentation system on, i.e., electric field generation device 120 in fragmentation region 118 placed in service. Second trace 314 includes a nitrate ($NO_3^-$) peak 316 as a result of the decomposition of EGDN, such peak indicative of the presence of EGDN. Notably, M.$Cl^-$ adduct peak 310 is not found with second trace 314 since the M.$Cl^-$ ions were decomposed using the fragmentation system. The peak just to the left of nitrate peak 316 is at least partially due to some additional $Cl^-$ from peak 308. Therefore, use of the fragmentation system during sample analysis in conjunction with the remainder of the tandem reactive dual drift tube and dual shutter configuration 112 significantly improves the sample analyses for substances of interest, such as EGDN.

Figure 4:
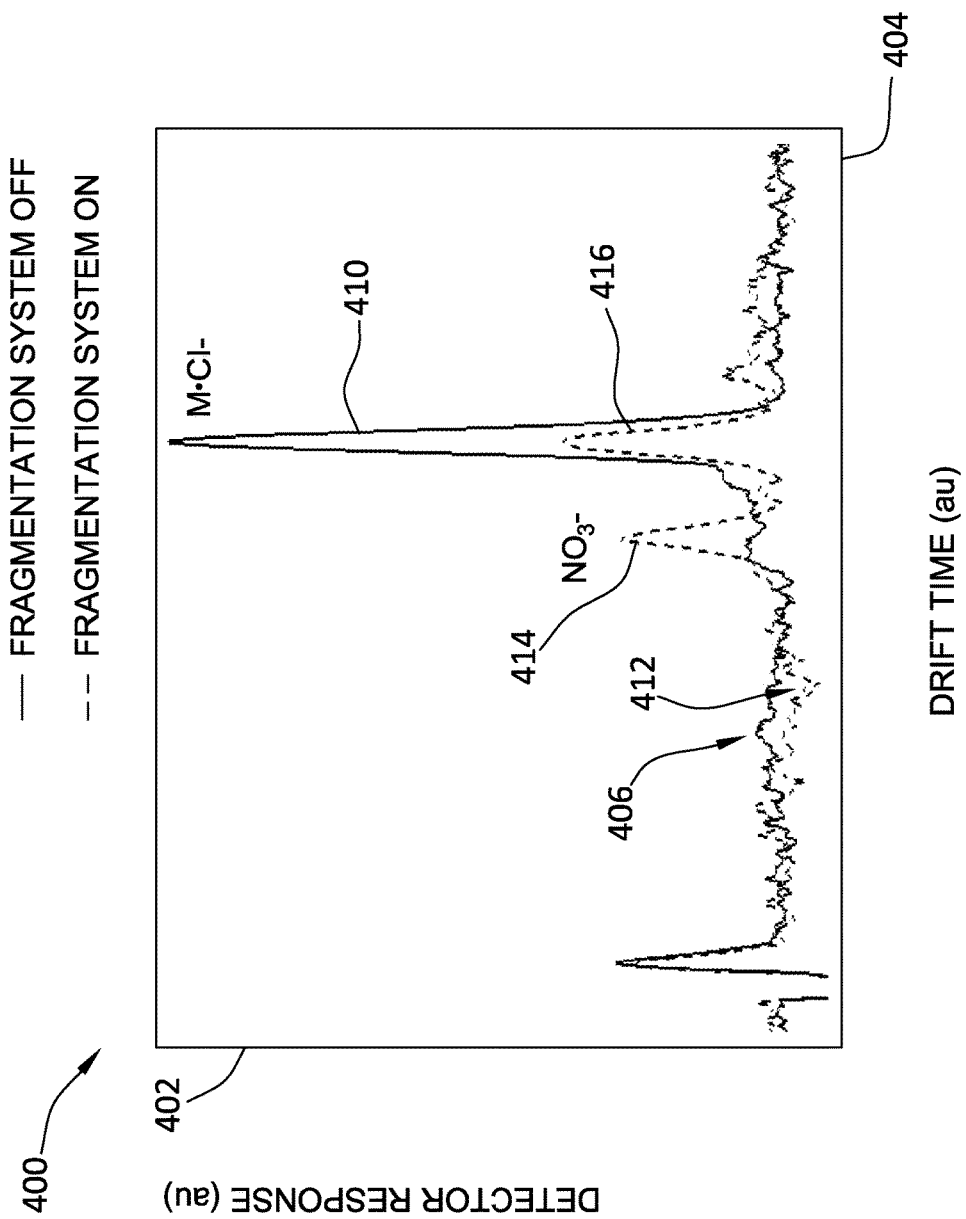

FIG. 4 is another graphical view, i.e., graph 400 of exemplary spectra that may be produced using ITMS detection systems 100 and 200 (shown in FIGS. 1 and 2, respectively). Graph 400 includes a y-axis 402 representative of ion intensity, i.e., detector response in arbitrary units (au). Also, graph 400 includes an x-axis 404 representative of drift time in arbitrary units (au). In the exemplary embodiment, a sample of ethylene glycol dinitrate (EGDN) [$C_2H_4(ONO_2)_2$], a common constituent of explosive devices, is introduced into IMS detection system 200, system 200 including tandem reactive drift tube configuration 112 (shown in FIGS. 1 and 2). Only the analyte ions of EGDN (shown as 310 in FIG. 3), however, are transferred through the first shutter 128 into the second drift tube 130 defining the second drift region 132 whereas all other ions of different mobilities are excluded from passing the shutter.

Graph 400 includes a first trace 406 representing a spectral analysis of the analyte ions of the EGDN sample with the fragmentation system off, i.e., electric field generation device 120 in fragmentation region 118 (both shown in FIGS. 1 and 2) removed from service. First trace 406 includes an M.$Cl^-$ adduct peak 410, peak 410 may indicate the presence of EGDN (EGDN*$Cl^-$). No other peaks such as the dopant peak previously shown as 308 in FIG. 3 are detected in the spectrum 406 displayed in FIG. 4.

Graph 400 also includes a second trace 412 representing a spectral analysis of the analyte ions (M.Cl)$^-$ of the EGDN sample with the fragmentation system on, i.e., electric field generation device 120 in fragmentation region 118 placed in service. Second trace 412 includes a nitrate ($NO_3^-$) peak 414 as a result of the decomposition of the analyte ions of EGDN, such peak indicative of the presence of EGDN. Notably, this peak was not present when the fragmentation system was off. Moreover, the intensity of a M.$Cl^-$ adduct peak 416 is much lower with second trace 412 compared to the intensity of 410 since the M.$Cl^-$ ions were decomposed using the fragmentation system. Therefore, use of the fragmentation system during sample analysis in conjunction with the remainder of the tandem reactive dual drift tube and dual shutter configuration 112 significantly improves the sample analyses for substances of interest, such as EGDN.

ITMS detection systems 100 and 200 (shown in FIGS. 1 and 2, respectively) facilitate ion fragmentation that further facilitates identifying chemical families primarily based on the way the analyte ions fragment. In general, ions in a gas phase at ambient pressure are not as robust as molecules in air at ambient pressure, i.e., the electrostatic charge on the ions increase the vulnerability of the bonds in the ion to weakening. Also, in general, increasing the thermal energy of the ions increases the vibratory motion, thereby further weakening the covalent bonds of the ions and, in cooperation with destabilizing effects of the ionic charge, rendering the bonds unstable until covalent bond cleavage, i.e., ion fragmentation is achieved. One method of increasing the temperature of the gaseous ions is through adding thermal energy to the gas by increasing the gas temperature through a heating device (not shown) to preheat the gas prior to injection into systems 100 and 200. Another method includes using the electric fields induced as described above to rapidly increase the kinetic energy of the ions that translates into increasing the thermal energy, and as such, the vibration of the ions. Use of the electric fields already present facilitates weakening of the ion bonds at much lower temperatures. Increasing the strength of the electric fields accelerates ion fragmentation. Because substances of a given family have similar molecular structures and similar bonding and ionic characteristics within the core structure of the molecule, such ions therefore tend to break into pieces corresponding to the characteristics of such substance(s). As such, further fragmentation of the ions into selected and known ion fragments further facilitates identifying chemical families.

The portable, atmospheric pressure, tandem reactive IMS devices described herein provide cost-effective systems and methods for improving detection of materials of interest from an object or person. The systems and methods described herein use a detector having two sequentially arranged drift tubes which are separated by shutters facilitating ions of a user-selected, i.e., library-defined drift time to be introduced into the second drift tube whereas other ions of a different mobility are discarded as needed. The IMS and ITMS devices disclosed herein facilitate multiple opportunities to isolate ions of interest including ion separation and selection in the first drift tube, predetermined modification through fragmentation through a controllable electric field, and selected transmission into the second drift tube ultimately ending with specific identification of the ions. Regulation of the electric field strength and temperature analyte ions from one compound may dissociate and form dissociation products that can further be characterized, while ions from another compound may dissociate as well but form different products or may even not dissociate at all. As such, this dissociation information is important for providing another dimension of characterizing the mobility of ions by their stability and their dissociation products which provides additional confidence in the presence or absence of peaks that facilitates determining if an alarm could be generated or rejected. The results are more easily interpreted and provide more definitive information that can be used for the characterization of ions since only ions of a particular drift time are exposed to the high electric field and the associated fragmentation. Consequently substantially all dissociation products detected in the second drift tube originate from the ions selected from the first drift tube and subsequently fragmented. Moreover, the additional optional introduction of dopants facilitates further modification of the selected ions through chemical reactions with or without dissociation. As such, the systems described herein facilitate an additional level of selectivity that dramatically reduces the false alarm rate from that observed on traditional IMS and ITMS systems. Therefore, the portable mobility spectrometers described herein facilitate substance analysis with higher confidence while maintaining atmospheric pressure operation.

A technical effect of the systems and methods described herein includes at least one of: (a) substantially decreasing the frequency of false alarms in TOF-IMS and -ITMS detection systems; (b) facilitating ions of a user-selected, i.e., library-defined drift time to be introduced into a second drift tube where other ions of a different mobility are discarded as needed; (c) executing predetermined modification of selected ions through fragmentation with a controllable electric field; (d) regulating the electric field strength and temperature such that analyte ions from one compound dissociate and form dissociation products that can further be characterized while ions from other compounds either dissociate and form different products or not dissociate at all; (e) increasing dissociation information for further characterizing the mobility of ions by their stability and their dissociation products; (f) increasing confidence in the presence or absence of peaks that facilitates determining if an alarm could be generated or rejected; and (g) weakening ionic bonds through leveraging weakening of such bonds due to the electrostatic charge of the ion and increased thermal energy of the ion until ion fragmentation into the predetermined ion fragments is achieved, thereby further facilitating identifying chemical families primarily based on the way the analyte ions fragment.

Although specific features of various embodiments of the invention may be shown in some drawings and not in others, this is for convenience only. In accordance with the principles of the invention, any feature of a drawing may be referenced and/or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for detecting constituents in a sample, said apparatus comprising:
   a first drift tube defining a first drift region;
   a second drift tube defining a second drift region;

an ion detector positioned downstream of said second drift region;

a controllable electric field device coupled to said first drift tube and said second drift tube, said controllable electric field device at least partially defining a fragmentation region;

a first ion shutter positioned between said first drift region and said fragmentation region;

a spectral analysis device coupled to said ion detector, said spectral analysis device configured to generate a detection spectrum representative of ions detected at said ion detector; and a control system coupled to said controllable electric field device and said first ion shutter, said control system comprising a processor, said control system configured to facilitate injection of a selected portion of the predetermined fragmented ions into said second drift region, said control system further configured to:

regulate said first ion shutter a first predetermined temporal period, thereby facilitating injection of a selected portion of ions from said first drift region into said fragmentation region; and regulate said controllable electric field device to modify the selected portion of ions to generate predetermined ion fragments within said fragmentation region.

2. The apparatus in accordance with claim 1, wherein said control system configured to regulate said first ion shutter a first predetermined temporal period is further configured to facilitate discarding a non-selected portion of ions to reduce injection of the non-selected portion of ions into said fragmentation region.

3. The apparatus in accordance with claim 2, wherein said control system configured to regulate said controllable electric field device to modify the selected portion of ions to generate predetermined ion fragments within said fragmentation region is further configured to regulate said controllable electric field device to dissociate a first portion of the selected portion of ions into a first portion of the predetermined ion fragments for further transmission to said second drift region.

4. The apparatus in accordance with claim 3, wherein said control system configured to regulate said controllable electric field device to modify the selected portion of ions to generate predetermined ion fragments within said fragmentation region is further configured to regulate said controllable electric field device to dissociate non-selected ions into fragments for discarding.

5. The apparatus in accordance with claim 3, wherein said control system configured to regulate said controllable electric field device to modify the selected portion of ions to generate predetermined ion fragments within said fragmentation region is further configured to regulate said controllable electric field device to not dissociate non-selected ions into fragments.

6. The apparatus in accordance with claim 3, wherein said control system configured to regulate said controllable electric field device to modify the selected portion of ions to generate predetermined ion fragments within said fragmentation region is further configured to regulate said controllable electric field device to facilitate weakening of ion bonds in cooperation with an electrostatic charge of each ion of the selected portion of ions until ion fragmentation into the predetermined ion fragments is achieved.

7. The apparatus in accordance with claim 1, wherein said apparatus is a time-of-flight (TOF) ion trap mobility spectrometer (ITMS) detection system, said apparatus further comprising:

a casing;

an ionization chamber at least partially defined by said casing, said ionization chamber configured to generate and store ions, said ionization chamber communicatively coupled to said control system; and a retaining grid coupled in flow communication with said ionization chamber and said first drift region, said retaining grid at least partially defining an ion trap, said control system further configured to regulate ion transmission into said first drift region through said retaining grid and through pulsing said ionization chamber.

8. The apparatus in accordance with claim 1, wherein said apparatus is a time-of-flight (TOF) ion mobility spectrometer (IMS) detection system, said apparatus further comprising:

a casing;

an ionization chamber at least partially defined by said casing, said ionization chamber configured to generate and store ions, said ionization chamber communicatively coupled to said control system; and an ion gate device coupled in flow communication with said ionization chamber and said first drift region, said ion gate device further operably coupled to said control system, said control system further configured to regulate ion transmission into said first drift region through pulsing said ionization chamber and de-energizing said ion gate device.

9. The apparatus in accordance with claim 1 further comprising a second ion shutter positioned between said fragmentation region and said second drift region, wherein said control system is further coupled to said second ion shutter, said control system further configured to regulate said second ion shutter a second predetermined temporal period, thereby further facilitating injection of a selected portion of the predetermined fragmented ions into said second drift region.

10. The apparatus in accordance with claim 1 further comprising an ion trap positioned between said fragmentation region and said second drift region, wherein said control system is further coupled to said ion trap, said control system further configured to regulate said ion trap a second predetermined temporal period, thereby further facilitating injection of a selected portion of the predetermined fragmented ions into said second drift region.

11. A method of detecting constituents in a sample, said method comprising:

channeling a sample gas stream to be tested for constituents into an ionization region;

generating a plurality of ions in the ionization region;

injecting at least a portion of the ions from the ionization region into a first drift region;

injecting a selected portion of ions from the first drift region into a fragmentation region comprising regulating a first ion shutter a first predetermined temporal period, the first ion shutter positioned between the first drift region and the fragmentation region; and modifying the selected portion of ions, thereby generating predetermined ion fragments within the fragmentation region comprising regulating a controllable electric field device positioned within the fragmentation region.

12. The method in accordance with claim 11 further comprising injecting a dopant into the fragmentation region and mixing at least a portion of the injected dopant with the selected portion of ions from the first drift region.

13. The method in accordance with claim 11, wherein regulating a first ion shutter a first predetermined temporal period comprises discarding a non-selected portion of ions, thereby reducing injection of the non-selected portion of ions into the fragmentation region.

14. The method in accordance with claim 13, wherein regulating the controllable electric field device positioned within the fragmentation region comprises regulating the controllable electric field device to dissociate a first portion of the selected portion of ions into a first portion of the predetermined ion fragments for further transmission to the second drift region.

15. The method in accordance with claim 14, wherein regulating the controllable electric field device positioned within the fragmentation region further comprises dissociating non-selected ions into fragments for discarding.

16. The method in accordance with claim 14, wherein regulating the controllable electric field device positioned within the fragmentation region further comprises not dissociating non-selected ions into fragments.

17. The method in accordance with claim 14, wherein regulating the controllable electric field device positioned within the fragmentation region further comprises weakening ion bonds in cooperation with an electrostatic charge of each ion of the selected portion of ions until ion fragmentation into the predetermined ion fragments is achieved.

18. The method in accordance with claim 11, wherein injecting at least a portion of the ions from the ionization region into a first drift region comprises:
    storing the ions in the ionization region; and
    regulating ion injection into the first drift region through a retaining grid comprising pulsing the ionization region.

19. The method in accordance with claim 11, wherein injecting at least a portion of the ions from the ionization region into a first drift region comprises:
    storing the ions in the ionization region; and
    regulating ion injection into the first drift region through pulsing the ionization chamber comprising de-energizing an ion gate device.

20. The method in accordance with claim 11 further comprising transmitting the selected portion of the predetermined fragmented ions through the second drift region to an ion detector.

21. The method in accordance with claim 20 further comprising generating a detection spectrum representative of the ions detected at the ion detector through a spectral analysis device coupled to the ion detector.

22. The method in accordance with claim 20, wherein transmitting the selected portion of the predetermined fragmented ions through the second drift region comprises regulating a second ion shutter a second predetermined temporal period, the second ion shutter positioned between the second drift region and the fragmentation region.

23. The method in accordance with claim 20, wherein transmitting the selected portion of the predetermined fragmented ions through the second drift region comprises regulating an ion trap a second predetermined temporal period, the ion trap positioned between the second drift region and the fragmentation region.

24. An apparatus for detecting constituents in a sample, said apparatus comprising:
    a first drift tube defining a first drift region;
    a second drift tube defining a second drift region;
    a controllable electric field device coupled to said first drift tube and said second drift tube, said controllable electric field device at least partially defining a fragmentation region;
    a first ion shutter positioned between said first drift region and said fragmentation region;
    a dopant injection conduit coupled in flow communication with said fragmentation region; and
    a control system coupled to said controllable electric field device and said first ion shutter, said control system comprising a processor, said control system configured to facilitate injection of a selected portion of the predetermined fragmented ions into said second drift region, said control system further configured to:
    regulate said first ion shutter a first predetermined temporal period, thereby facilitating injection of a selected portion of ions from said first drift region into said fragmentation region; and
    regulate said controllable electric field device to modify the selected portion of ions to generate predetermined ion fragments within said fragmentation region.

* * * * *